United States Patent [19]

Sesekura et al.

[11] Patent Number: 5,680,872
[45] Date of Patent: Oct. 28, 1997

[54] SIMPLE BLOOD-COLLECTING DEVICE

[75] Inventors: Tetsuya Sesekura, Yokohama; Junichi Watanuki, Tokyo, both of Japan

[73] Assignee: Kabushiki Kaisya Advance, Tokyo, Japan

[21] Appl. No.: 406,902

[22] PCT Filed: Aug. 9, 1994

[86] PCT No.: PCT/JP94/01317

§ 371 Date: Mar. 29, 1995

§ 102(e) Date: Mar. 29, 1995

[87] PCT Pub. No.: WO95/04500

PCT Pub. Date: Feb. 16, 1995

[30] Foreign Application Priority Data

Aug. 10, 1993 [JP] Japan ................................ 5-216888

[51] Int. Cl.$^6$ ................................................ A61B 5/00
[52] U.S. Cl. .............................. 128/760; 128/770; 606/182
[58] Field of Search ................................. 128/762, 763, 128/764, 770, 635; 604/90, 201, 176, 134; 606/181, 182; 364/413.07

[56] References Cited

U.S. PATENT DOCUMENTS

| 4,653,513 | 3/1987 | Dombrowski | 128/765 |
| 5,054,499 | 10/1991 | Swierczek | 128/770 |
| 5,153,828 | 10/1992 | Inoue et al. | 364/413.07 |

FOREIGN PATENT DOCUMENTS

| 0 103 664 | 3/1984 | European Pat. Off. |
| 0 555 554 | 8/1993 | European Pat. Off. |
| 3 708 031 | 11/1987 | Germany |
| 62-38140 | 2/1987 | Japan |
| 3-60645 | 3/1991 | Japan |
| 92/11879 | 7/1992 | WIPO |

OTHER PUBLICATIONS

Patent Abstracts of Japan vol. 16, No. 507, Jun. 07 1992.

*Primary Examiner*—Max Hindenburg
*Assistant Examiner*—Pamela L. Atwood
*Attorney, Agent, or Firm*—Foley & Lardner

[57] ABSTRACT

A blood-collecting device comprising a decompression chamber, a suction cell with paracentetic means, and paracentesis-terminating means. Simple and painless blood collection is made possible.

21 Claims, 2 Drawing Sheets

5,680,872

SIMPLE BLOOD-COLLECTING DEVICE

TECHNICAL FIELD

The present invention relates to a simple blood-collecting device. Specifically, it relates to a simple blood-collecting device which allows one to collect one's own blood.

BACKGROUND ART

In recent years, which have seen an increase in the number of patients suffering from various adult diseases such as diabetes, believed to be due to changes in eating habits and a greater level of stress, a heavy burden is being imposed on the daily lives of the patients themselves who must make regular visits to the hospital, and therefore as blood sugar tests become an ever more usual part of their daily lives, the procedure of blood collection itself is receiving more attention as an important topic. The problem of the pain accompanying blood collection becomes a more significant issue in cases where the procedure must be repeated, and it is becoming a serious obstacle particularly for insulin-dependent patients, which include a large number of children. Furthermore, the infection of patients via blood has become a social problem in recent years, and therefore, in the interest of preventing especially serious diseases such as AIDS and hepatitis, a device has been sought which may allow patients to take repeated blood collections by themselves without undue burden.

DISCLOSURE OF THE INVENTION

Nevertheless, no device has been proposed yet which allows painless and simple collection of blood.

In light of the prior art, the present invention is aimed at providing a device which allows blood to be collected in a painless, reliable manner, which is a blood-collecting device comprising a decompression chamber, a skin suction portion, paracentetic means and paracentesis-terminating (withdrawal) means.

Because this blood-collecting device has a very simple construction, is compact and lightweight and uses no special parts, it is economical and may be used in a disposable manner.

BEST MODE FOR CARRYING OUT THE INVENTION

Figure 1A:
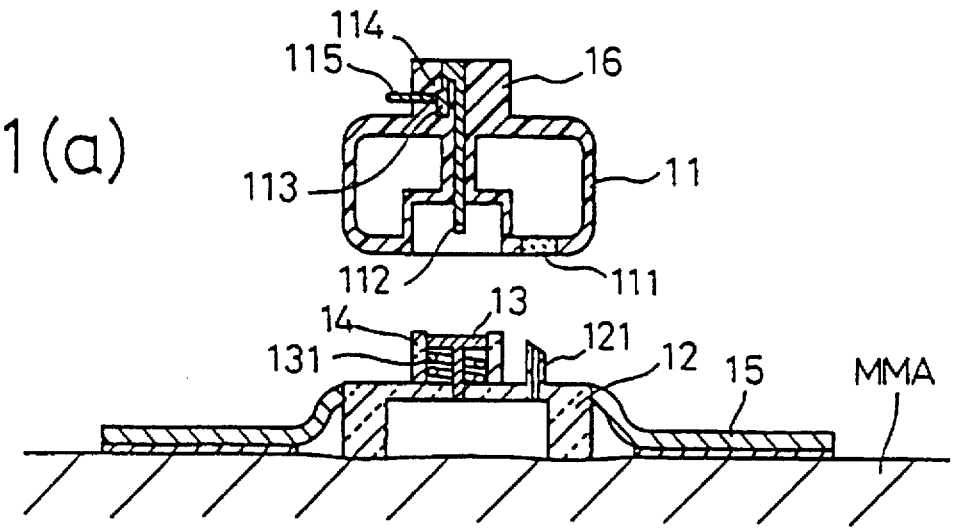
FIGS. 1(a) to 1(d) are cross-sectional sketches of an embodiment of the device according to the present invention in its states of operation.

The characteristics of the present invention are as follows. Decompression suction is concentrated on a local surface of the skin. As this local decompression suction is induced, the inner surface of the skin becomes congested with blood, causing enlargement and swelling of the epidermis. This swollen skin comes into contact with the paracentetic means preset at a prescribed position. Because the swollen skin is in a sufficiently enlarged state, the paracentetic means easily penetrates the skin (epidermis, etc.). After a certain period of time, a terminating procedure is performed to withdraw the paracentetic means, and decompression suction is again initiated.

During the process of decompression suction, the section closed by the penetrating section (tip) of the paracentetic means is opened when the paracentetic means is drawn out from the skin, allowing the blood to flow out. Because of the local suction, no pain is felt even when the paracentetic means pierces the skin, since that is offset by the irritation of the suction.

According to the present invention, the decompression chamber is a means for creating suction at the surface of the skin, and typically performs the decompression function either mechanically and chemically, manually or automatically, etc., though it is not particularly restricted. An example of a decompression chamber may be an ampule- or cassette-like piece preformed in a decompressed state using an airtight material; or a device which creates a suction effect by inducing temperature changes in a molecular sieve. Also, examples of paracentetic means include, in either plural or single form, needles, hollow needles, dentate-sided needles, acupuncture/moxibustion needles and microblades.

The length of the paracentetic means is preferably a few hundred micrometers to a few millimeters, but it is not particularly restricted. The paracentetic means should also be situated either at the center or peripheral part of the suctioning section so that the phenomenon of swelling of the epidermis by decompression suction can be used to allow efficient penetration of the epidermis without causing pain.

The paracentesis-terminating means is means for removing the paracentetic means when it has penetrated the skin, and it operates mainly within a certain time during the decompression suction. The operation for termination of the paracentesis is, for example in the case of paracentesis with a needle, withdrawal of the needle.

There are a variety of constructions for removal of the paracentetic means, and as an example there may be mentioned a construction in which the paracentetic means is removed manually, or a construction which automatically performs a series of operations including all or part of the paracentesis-terminating and even the suction operation.

The paracentesis is terminated once the decompression suction has been stopped, and decompression suction may then once again be initiated. The means for resuming the decompression suction may even be a different means than that which performs the initial decompression suction.

Examples of the present invention are explained below, with reference to the accompanying drawings.

FIGS. 1(a) to 1(d) are cross-sectional drawings of an embodiment of the device according to the present invention in its states of operation.

Here, 11 is a decompression chamber which encloses a decompressed space. A control section A 16 is situated on the decompression chamber 11. 111 is a membrane section, which consists of rubber, plastic or the like and has a prescribed strength. Reference 112 is a pressing rod which slides up and down. The pressing rod 112 is constructed so as to slide up and down in the decompression chamber, but the area in which the pressing rod 112 slides and the decompressed space of the decompression chamber 11 are mutually isolated. At the upper end of the pressing rod 112 there is provided a latch A 113 with flexibility in the diametrical direction. Reference 114 is a latch B which is situated so as to be anchored at one location along the sliding path of the latch A 113 along the wall of the control section A 16 surrounding the pressing rod 112. Reference 115 is a pressing switch, one end of which is situated outside the control section A 16 and the other end of which is situated within the wall of the control section A 16 on which the pressing rod 112 slides. The pressing switch 115 functions so that when the one end thereof is pressed, the other end protrudes through the inner wall, thus placing the other end within the inner wall after pressing.

Reference 12 is a suction cell which is open at the bottom, i.e. at the side of contact with the skin. One or a plurality of holes are formed at the top of the suction cell 12, which connect with a hollow needle 121 for communication with the decompression chamber 11. In the section at the bottom of the suction cell 12 which contacts the skin there is situated a material such as rubber or plastic which has a high degree of friction with the skin, in order to prevent movement of the skin, and this may be provided in a slightly protruding shape. Reference 13 is paracentetic means which is made of a fine needle with an aperture of 0.3 mm and flat at the upper end, and which is located outside the top of the suction cell 12, passing through a helical spring 131 contained thereby. There are no particular restrictions on the position of the paracentetic means 13, the position of the holes or the aperture of the fine needle.

Reference 14 is a control section B which defines the periphery of the spring 131 and the paracentetic means 13. An elastic material such as rubber may be used in place of the spring 131, or there may be employed an electromagnetic force or decompressive suction force generated from the decompression chamber.

Reference 15 is an adhesive material, which may consist of an adhesive material layer placed over a support material formed as concentrically ringed films of flexible plastic, rubber or paper materials.

The device operates in the following manner when used.

First, the adhesive material 15 is placed face-down at a site on the skin (MMA) from which the blood is to be collected. The adhesive layer section of the adhesive material 15 bonds to the skin (MMA), becoming anchored to the surface of the skin, and the suction cell 12 thus becomes sealed in the manner shown in FIGS. 1(a).

In the control section A 16, the pressing rod 112 has already been pressed downward and the latch A 113 and latch B 114 are interlocked.

The decompression chamber is fitted over the suction cell 12 in a position where the hollow needle 121 meets the membrane section 111. When the hollow needle tears through the membrane section 111, the decompressed space becomes connected with the interior of the suction cell 12, and the suction cell 12 begins exert a suction action on the skin.

Also, because the pressing rod 112 pushes down the paracentetic means 13, the tip of the paracentetic means 13 protrudes in through the upper side of the suction cell 12 while the spring 131 is compressed.

Figure 1B:
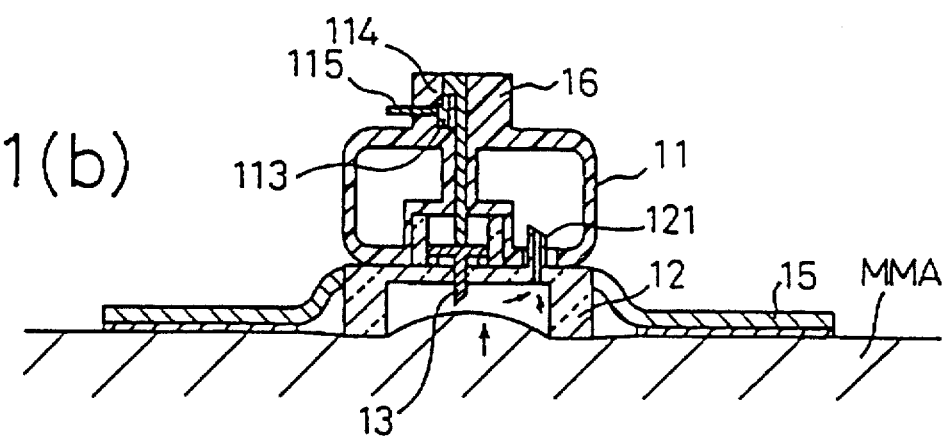
Figure 1C:
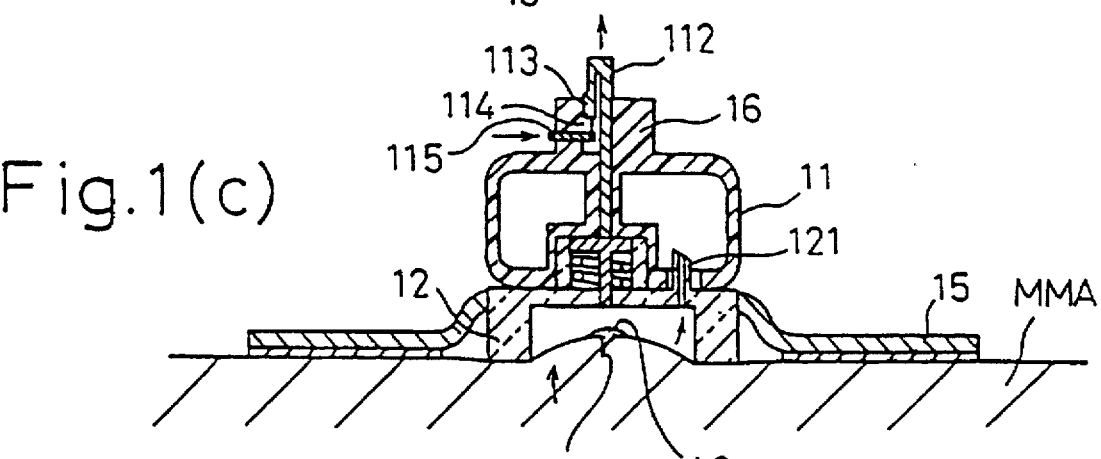
Figure 1D:
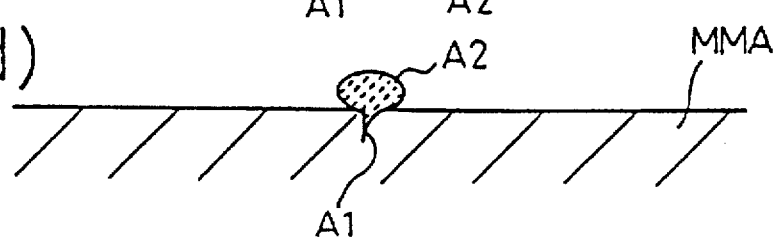

The suction action of the suction cell 12 causes body fluid in the skin (MMA) including blood to become congested, and the skin under the suction cell 12 begins to swell, as shown in FIG. 1(b). In this figure, the swelling of the skin is not sufficient to contact the paracentetic means 13, but the skin eventually swells greatly enough to contact the paracentetic means 13 and continues to swell a certain degree thereafter as well. This section of the skin becomes locally stretched since it is held around the circumference of the suction cell 12, and therefore the paracentetic means 13 easily penetrates the epidermis of the skin (MMA). In this case, the contact surface of the suction cell 12 with the skin which prevents movement of the skin as explained earlier further promotes stretching of the swelled area. The paracentetic means 13 penetrates the skin, but the penetrating part, or tip, of the paracentetic means 13 causes a closure to the flow of blood.

After a certain period of time, the pressing switch 115 is pressed. The other end of the pressing switch 115 pushes the latch A 113 inward, causing the latch A 113 to move inward thus releasing the interlocked state of the latch A 113 and the latch B 114. The release of the interlock causes the compressed spring 131 to rebound, pulling up the paracentetic means 13. Thus, since the paracentetic means 13 is pulled up toward the top, it is withdrawn from the surface of the skin to expose the penetrated site A1. Blood and body fluid A2 flow out from the penetrated site A1 due to the withdrawal of the paracentetic means 13 and the suction action from the decompression chamber 11 (FIG. 1(c)). Blood also flows out when the device is removed from the surface of the skin (MMA), as shown in FIG. 1 (d). The amount of blood is about 10 to 30 μL. The flowed out blood may be subjected to a testing instrument after being impregnated on test paper or taken with a dropper or the like. In the above example, the terminating means consists of the control sections A 16 and B 14 which are manually operated, but a variety of other constructions may be employed for the termination including, for example, one in which the withdrawal of the paracentetic means is performed by manual rotary action. In addition to manual termination, a series of operations for suction, termination and subsequent suction may be performed automatically.

Appropriate selection is made of the time waited for congestion and the time until penetration of the skin with the paracentetic means, after suction of the skin. Incidentally, there is no particular need to wait for congestion during the use of this device, as the operation according to the present invention is sufficiently carried out by at least penetrating the skin with the paracentetic means after the skin has become stretched due to swelling after suction, and terminating the operation by withdrawal of the paracentetic means. If carried out quickly, 20 to 30 seconds is adequate for this series of operations. For example, a suction time of about 10 to 60 seconds, a penetration time of about 0.1 to 1 second and a suction time after termination of penetration of about 10 to 20 seconds is possible.

Figure 2:
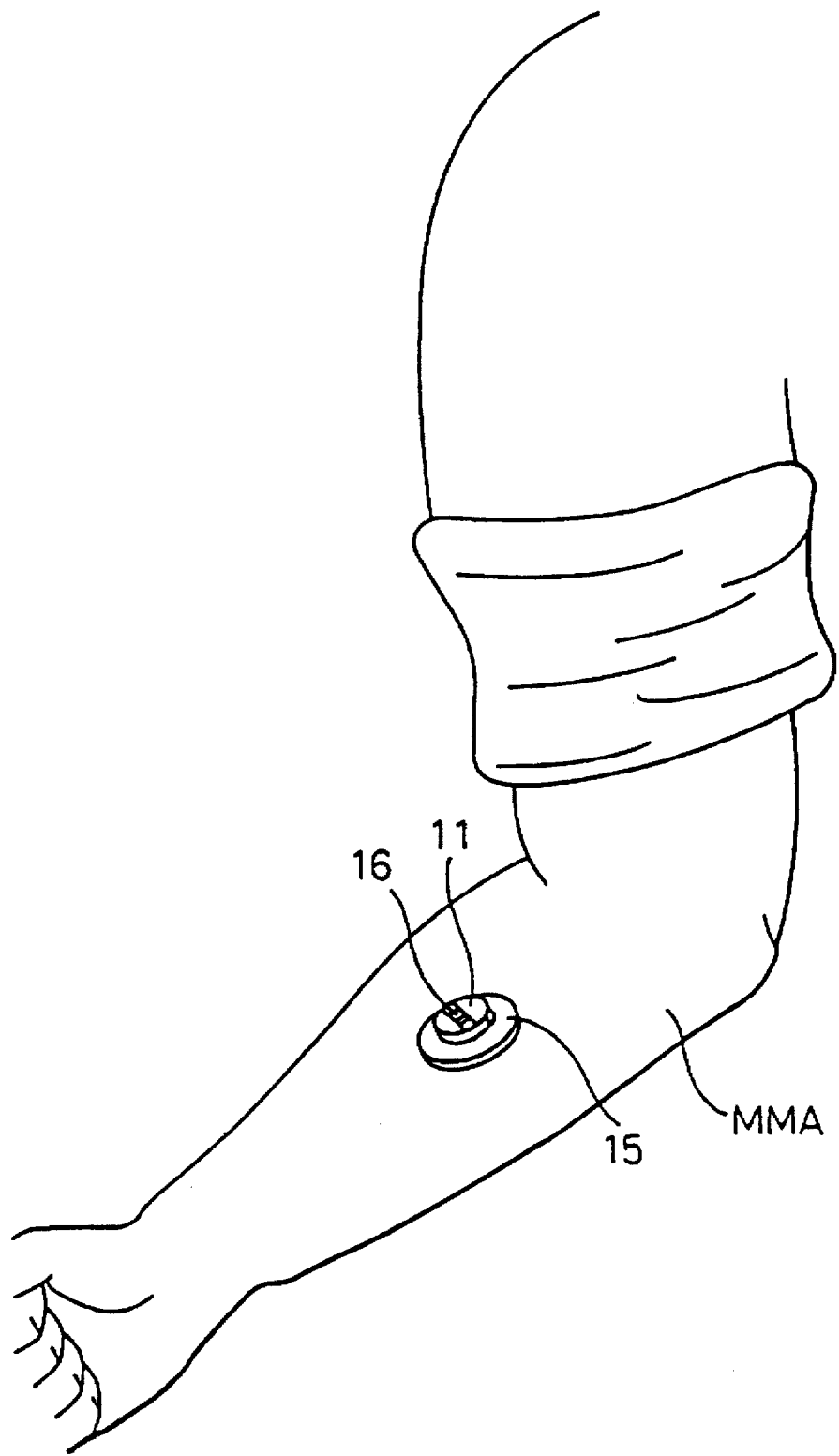
FIG. 2 is a drawing showing the device of FIG. 1 in a state of use.

FIG. 2 shows the above-mentioned device adhered to the upper arm of the body. Reference 11 is the decompression chamber, 15 is the adhesive section, and 16 is the control section A. Because the device is small and lightweight, it may be used in the adhered manner shown in FIG. 2. However, the adhesive section need only be employed when appropriate, and the device may even have no adhesive section, to be used in a handheld manner. If the blood collection time is shorter, it is more convenient not to use an adhesive material.

INDUSTRIAL APPLICABILITY

The device of the present invention is small, lightweight and inexpensive to manufacture, and is therefore suitable as a disposable type, and because it allows blood to be collected in a reliable manner it is extremely useful in a practical sense.

We claim:

1. A blood-collecting device comprising:
   a decompression chamber;
   a suction cell separate from said decompression chamber, with paracentric means;
   said suction cell contacting a skin surface to form a closed space, and communicating with said decompression chamber to cause decompression of said suction cell;
   said paracentric means extending within said suction cell initially spaced from said skin surface;

said paracentric means subsequently contacting and penetrating said skin surface; and paracentesis-terminating means for withdrawal of said paracentric means from said skin surface.

2. The device according to claim 1, wherein the decompression chamber comprises an ampule or cassette preformed in a decompressed state using an airtight material.

3. The device according to claim 1, wherein the decompression chamber comprises a device which creates a suction effect by inducing temperature changes in a molecular sieve.

4. The device according to claim 1, wherein the paracentetic means is one selected from needles, hollow needles, dentate-sided needles, acupuncture/moxibustion needles and microblades.

5. The device according to claim 4, wherein the paracentetic means has a length of a few hundred micrometers to a few millimeters.

6. The device according to claim 1, wherein the paracentetic means is housed at the top of the suction cell, and when used is operated to protrude into the suction cell by pressing force from above.

7. The device according to claim 1, wherein the suction cell, when used, connects with the decompression chamber causing suction by the reduced pressure of the decompression chamber.

8. The device according to claim 7, wherein the connection between the suction cell and the decompression chamber is established by tearing through a membrane provided on the decompression chamber with a hollow needle provided on the suction cell.

9. The device according to claim 1, wherein the paracentesis-terminating means is operated by the action of a resilient material to withdraw the paracentetic means penetrating the skin.

10. A blood collecting device comprising:

a sealed decompression chamber;

a suction cell separate from said decompression chamber and adapted for mating with said decompression chamber; and a skin perforator extending within said suction cell to pierce a skin surface.

11. A blood collecting device as claimed in claim 10, further comprising skin perforator release means on one of said suction cell or said decompression chamber.

12. A blood collecting device as claimed in claim 10, wherein said suction cell and said decompression chamber are separate components.

13. A blood collecting device as claimed in claim 10, wherein suction cell forms an airtight seal with a skin surface.

14. A blood collecting device as claimed in claim 10, further comprising an adhesive material around said suction cell.

15. A blood collecting device as claimed in claim 10, further comprising at least one hollow needle extending from said suction cell.

16. A blood collecting device as claimed in claim 15, wherein said decompression chamber further comprises a mating face adapted to mate with said suction cell.

17. A blood collecting device as claimed in claim 16, wherein said decompression chamber further comprises a membrane extending along a portion of said mating face.

18. A blood collecting device as claimed in claim 17, wherein said hollow needle of said suction cell pierces said membrane of said decompression chamber upon mating of said suction cell with said decompression chamber.

19. A blood collecting device as claimed in claim 10, wherein a pressing rod extends through said a center of said decompression chamber and drives said skin perforator upon mating of said compression chamber with said suction cell.

20. A blood collecting device as claimed in claim 10, wherein said skin perforator release means comprises a helical spring.

21. A method of blood collection comprising:

adhering a suction cell to a skin surface in an airtight manner;

mating said suction cell with a decompression cell;

piercing a membrane of said decompression chamber with a hollow needle of said suction cell to form a positive vacuum in said suction cell upon partial mating of said suction cell with said decompression chamber;

driving a skin perforator extending into said suction cell with a pressing rod of said decompression chamber upon partial mating of said suction cell with said decompression chamber;

swelling said skin surface to contact said skin perforator; and piercing said skin surface with said skin perforator upon full mating of said suction cell with said decompression chamber.

* * * * *